United States Patent [19]

Abichandani et al.

[11] Patent Number: 5,516,956
[45] Date of Patent: May 14, 1996

[54] DUAL BED XYLENE ISOMERIZATION

[75] Inventors: Jeevan S. Abichandani, Voorhees; Chaya R. Venkat, Princeton, both of N.J.

[73] Assignee: Mobil Oil Corporation, Fairfax, Va.

[21] Appl. No.: 342,322

[22] Filed: Nov. 18, 1994

[51] Int. Cl.$^6$ .................................................. C07C 5/22
[52] U.S. Cl. ........................... 585/481; 585/475; 585/488; 585/486
[58] Field of Search ...................... 585/475, 481, 585/482, 486

[56] References Cited

U.S. PATENT DOCUMENTS

| | | | |
|---|---|---|---|
| Re. 31,782 | 12/1984 | Olson et al. | 585/481 |
| 4,090,981 | 5/1978 | Rodewald | 252/455 Z |
| 4,117,026 | 9/1978 | Haag et al. | 260/671 R |
| 4,163,028 | 7/1979 | Tabak et al. | 585/481 |
| 4,312,790 | 1/1982 | Butter et al. | 252/455 Z |
| 4,477,583 | 10/1984 | Rodewald | 502/71 |
| 4,560,820 | 12/1985 | Field | 585/489 |
| 4,582,815 | 4/1986 | Bowes | 502/64 |
| 4,783,568 | 11/1988 | Schmidt | 585/477 |
| 4,899,011 | 2/1990 | Chu et al. | 585/481 |
| 4,950,835 | 8/1990 | Wang et al. | 585/467 |
| 5,053,374 | 10/1991 | Absi et al. | 502/64 |
| 5,321,183 | 6/1994 | Chang et al. | 585/475 |
| 5,349,114 | 9/1994 | Lago et al. | 585/475 |
| 5,365,003 | 11/1994 | Chang et al. | 585/470 |
| 5,365,004 | 11/1994 | Beck et al. | 585/475 |
| 5,367,099 | 11/1994 | Beck et al. | 585/475 |
| 5,371,312 | 12/1994 | Lago et al. | 585/475 |
| 5,382,737 | 1/1995 | Beck et al. | 585/475 |

*Primary Examiner*—Shrive Beck
*Assistant Examiner*—Timothy H. Meeks
*Attorney, Agent, or Firm*—Alexander J. McKillop; Malcolm D. Keen; Gerald L. Harris

[57] ABSTRACT

A mixture of aromatic hydrocarbons, comprising ethylbenzene and at least one xylene, is isomerized using a two component catalyst system to convert the ethylbenzene to compounds that may be removed from the aromatic hydrocarbon stream and to produce a product stream wherein the para-xylene concentration is approximately equal to the equilibrium ratio of the para-isomer. The first catalyst comprises an intermediate pore size zeolite that is effective for ethylbenzene conversion. The first catalyst is preferably silica-bound. The second catalyst comprises an intermediate pore size zeolite, which further has a small crystal size and which is effective to catalyze xylene isomerization. Each of the catalysts of this invention may contain one or more hydrogenation/dehydrogenation component.

40 Claims, No Drawings

ND BED XYLENE ISOMERIZATION

DUAL BED XYLENE ISOMERIZATION

FIELD OF THE INVENTION

This invention is directed to a process for xylene isomerization using a two catalyst system, wherein the first catalyst comprises a silica bound, intermediate pore size zeolite that, optionally, has been selectivated at least once to improve its ethylbenzene conversion selectivity and wherein the second catalyst is effective to catalyze xylene isomerization reactions.

BACKGROUND OF THE INVENTION

Since the announcement of the first commercial installations of Octafining in Japan in June, 1958, this process has been widely installed for the supply of para-xylene. See "Advances in Petroleum Chemistry and Refining", volume 4, page 433 (interscience Publishers, New York 1961). That demand for para-xylene has increased at remarkable rates, particularly because of the demand for terephthalic acid to be used in the manufacture of polyesters.

Para-xylene is a valuable chemical feedstock which may be separated for use in the synthesis of polyesters from mixed xylenes by fractional crystallization, among other methods. Benzene is a highly valuable product for use as a chemical raw material. Toluene is also a valuable product for use as a solvent, in chemical manufacturing processes, and as a high octane gasoline component.

Typically, para-xylene is derived from mixtures of $C_8$ aromatics separated from such raw materials as petroleum naphthas, particularly reformates, usually by selective solvent extraction. The $C_8$ aromatics in such mixtures and their properties are:

|  | Freezing Point °F. | Boiling Point °F. | Density Lbs./U.S. Gal. |
|---|---|---|---|
| Ethylbenzene | −139.0 | 277.1 | 7.26 |
| Para-xylene | 55.8 | 281.3 | 7.21 |
| Meta-xylene | −53.3 | 281.8 | 7.23 |
| Ortho-xylene | −13.8 | 291.2 | 7.37 |

Calculated thermodynamic equilibria for the $C_8$ aromatic isomers at 850° F. are:

| Wt. % Ethylbenzene | 8.5 |
|---|---|
| Wt. % Para-xylene | 22.5 |
| Wt. % Meta-xylene | 48.0 |
| Wt. % Ortho-xylene | 21.5 |
| TOTAL | 100.0 |

Principal sources of the mixtures of $C_8$ aromatics are catalytically reformed naphthas and pyrolysis distillates. The $C_8$ aromatic fractions from these sources vary quite widely in composition but will usually be in the range of 10 to 32 wt. % ethylbenzene (EB) with the balance, xylenes, being divided approximately 50 wt. % meta and 25 wt. % each of para and ortho.

Individual isomer products may be separated from the naturally occurring mixtures by appropriate physical methods. Ethylbenzene may be separated by fractional distillation, although this is a costly operation. Ortho-xylene may be separated by fractional distillation, and it is so produced commercially. Para-xylene may be separated from the mixed isomers by fractional crystallization, selective adsorption (e.g., the Parex process), or membrane separation.

As commercial use of para-xylene and ortho-xylene has increased, isomerization of the other $C_8$ aromatics to produce an equilibrium mixture of xylenes, and thus increase the yields of the desired xylenes, has become increasingly important. Octafining is one of the processes which produce an increased amount of xylenes.

In a typical plant utilizing the Octafining process, a mixture of $C_8$ aromatics is introduced to an ethylbenzene tower wherein the stream is stripped of a portion of its ethylbenzene content, to an extent consistent with retaining all of the xylenes in the feed stream without unduly expensive "superfractionation." Ethylbenzene is taken off as overhead, while a bottom stream, consisting principally of xylenes, together with a significant amount of ethylbenzene, passes to a xylene splitter column. The bottoms stream from the xylene splitter, comprising primarily ortho-xylene and $C_9$ aromatic, passes to the ortho-xylene tower from which ortho-xylene is taken off overhead, and heavy ends are removed. The overhead from the xylene splitter column is transferred to conventional crystallization separation. The crystallizer operates in the manner described in U.S. Pat. No. 3,662,013, incorporated by reference herein.

Because its melting point is much higher than that of the other $C_8$ aromatics, para-xylene is readily separated in the crystallizer after refrigeration of the stream, and a xylene mixture lean in para-xylene is transferred to an isomerization unit. The isomerization charge passes through a heater, is admixed with hydrogen, and the mixture is introduced to the isomerizer.

Isomerized product from the isomerizer is cooled and passed to a high pressure separator from which separated hydrogen can be recycled in the process. The liquid product of the isomerization passes to a stripper from which light ends are passed overhead. The remaining liquid product comprising primarily $C_8^+$ hydrocarbons is recycled in the system to the inlet of the xylene splitter.

It will be seen that the system is adapted to produce quantities of para-xylene from a mixed $C_8$ aromatic feed containing all of the xylene isomers plus ethylbenzene. The key to efficient operation to accomplish that result is the use of the isomerizer which takes crystallizer effluent lean in para-xylene and converts the other xylene isomers in part to para-xylene for further recovery at the crystallizer.

Among the xylene isomerization processes available in the art, Octafining was originally unique in its ability to convert ethylbenzene. Other xylene isomerization processes have required extremely expensive fractionation to separate ethylbenzene from other $C_8$ aromatic fractions. As will be seen in the table of properties above, the boiling point of ethylbenzene is very close to those of para-xylene and meta-xylene. Complete removal of ethylbenzene from the charge by conventional methods, e.g., distillation, is therefore impractical. The usual expedient for coping with the problem is an ethylbenzene separation column in the isomerizer-separator loop when using catalysts other than those used in Octafining. However, Octafining does not require this expensive auxiliary equipment to prevent build up of ethylbenzene in the loop. This advantageous feature is possible because the Octafining catalyst converts ethylbenzene to xylenes.

In Octafining, ethylbenzene reacts through ethyl cyclohexane to dimethyl cyclohexanes, which in turn equilibrate to xylenes. Competing reactions are disproportionation of ethylbenzene to ethane and benzene, and hydrocracking of alkyl cyclohexanes.

A significant improvement over the Octafining process arose with the introduction of zeolite catalysts, such as zeolite ZSM-5, combined with a metal, such as platinum, as described in U.S. Pat. No. 3,856,872. At temperatures of about 700° F.–800° F., ethylbenzene is converted by disproportionation over the ZSM-5 catalyst to benzene and diethylbenzene. At higher temperatures, and in the presence of ZSM-5 catalyst of reduced activity, ethylbenzene and other single ring aromatics are converted by splitting off side chains of two or more carbon atoms as described in U.S. Pat. No. 4,188,282.

These developments permit upgrading of Octafining reactors by the substitution of the improved (ZSM-5) catalyst.

In many processes for xylene isomerization, conversion of ethylbenzene is constrained by the need to hold conversion of xylenes to other compounds to acceptable levels. Thus, although the above described advances provide significant improvements over Octafining in this respect, operating conditions are still selected to balance the advantages of xylene loss by disproportionation and the like.

A further advance in the art is described in U.S. Pat. No. 4,163,028, incorporated by reference herein, which is directed to xylene isomerization and ethylbenzene conversion at high temperatures with a ZSM-5 zeolite of very high silica/alumina ratio, whereby the acid activity of the catalyst is reduced. Other patents also disclose the use of ZSM-5 zeolite catalysts with reduced acid activity for high temperature (800° F.) isomerization.

The inventions of those patents are predicated on discovery of combinations of catalyst and operating conditions which decouple ethylbenzene conversion from xylene loss in a xylene isomerization reaction, thus permitting the use of $C_8$ fractions which contain ethylbenzene as the feed, without sacrifice of xylenes at conditions which will promote adequate conversion of ethylbenzene. These results are obtained by the use of a catalyst characterized by ZSM-5 zeolite substantially reduced in activity, e.g., by dilution, steaming, very high silica/alumina ratio, base exchange with alkali metal, coking or the like. At the high temperatures of 800° F.–1000° F., the reduced activity zeolite exhibits effective power for isomerization of xylene and for splitting off alkyl side chains of two or more carbon atoms from single ring aromatics at long on-stream periods. The disproportionation activity of the zeolite is severely depressed by the reduced acid activity, resulting in low losses of xylene by that mechanism. That lack of disproportionation activity impairs the capacity of the catalyst to handle trialkyl aromatics of nine or more carbon atoms, e.g., trimethylbenzene, as practiced in some processes. It thus becomes necessary to remove from the recycle stream those components having more than eight carbon atoms to avoid excessive build-up in the system of $C_9$ and higher hydrocarbons. The catalyst also has the ability to crack paraffins in the charge to lower boiling compounds readily removable from recycle streams by fractionators normally present in the para-xylene recovery/isomerizer loop.

By reason of this combination of activities, the catalyst may used in a system charging reformate without removal of paraffin hydrocarbons, as described in U.S. Pat. No. 4,211,836.

U.S. Pat. No. 4,159,282 and Re. 31,782 to Olson et al., incorporated by reference herein, describe a xylene isomerization process in which a specified crystalline aluminosilicate zeolite characterized by a crystal size of at least about 1 micron is employed as an isomerization catalyst. In a more specific embodiment, the reaction is carried out with a crystalline aluminosilicate catalyst having a bimodal crystal size distribution generally falling in two ranges, less than about 1 micron and greater than about 1 micron with the latter being in major proportion.

The catalysts of zeolite, plus a metal, such as platinum, discussed above, are of the type known as "dual function catalysts" characterized by the provision of catalyst sites of different functions, each of which separately performs its function, often one step for each type of site in a multi-step reaction sequence. Such catalysts and the sequential reaction sites are discussed and explained by P. B. Weisz, "Polyfunctional Heterogeneous Catalysis," Advances in Catalysis, 13, pp 137–190 (1962). Weisz describes some experiments in which the two types of sites are provided by separate entities, such as physical mixtures of particles each of which provides only one type of catalytic site. Isomerization of certain paraffins over physical mixtures of acidic silica-alumina and platinum on a carrier is specifically described.

SUMMARY OF THE INVENTION

The process of this invention is directed to converting high percentages of the ethylbenzene present in mixed ethylbenzene-xylene containing feeds, while simultaneously minimizing xylene loss and converting xylenes to approximately the thermal equilibrium concentration. In this way, the volume of any recycle stream and/or complexity of the separation processes needed in a xylene recovery process are minimized.

One typical mode of ethylbenzene (EB) reduction is generally through transalkylation to benzene (BZ) and diethylbenzene (DEB). A representation of this reaction is given below:

$$EB+EB \rightarrow BZ+DEB \tag{1}$$

Another typical reaction for EB reduction is through dealkylation to BZ and ethylene (ETH). A representation of this reaction is given below:

$$EB \rightarrow BZ+ETH \tag{2}$$

The ethylene produced is very reactive and is quickly saturated to ethane Using hydrogen in the presence of a hydrogenation catalyst, such as platinum. Several undesirable side reactions may also take place, leading to xylene (XYL) loss. Representations for some of the major side reactions are given below:

$$EB+XYL \rightarrow BZ+DMEB \tag{3}$$

$$EB+XYL \rightarrow TOL+MEB \tag{4}$$

$$XYL+XYL \rightarrow TOL+TMB \tag{5}$$

$$ETH+XYL \rightarrow DMEB \tag{6}$$

where:
DMEB is dimethylethylbenzene
TOL is toluene
MEB is methylethylbenzene.

In the process of this invention, any reaction leading to ethylbenzene destruction or conversion is referred to herein as "ethylbenzene conversion." Of these reactions, reactions as depicted by equations 1 and 2 are desirable. Reactions as depicted in equations 3 through 6 along with similar and related types of reactions are undesirable and are collectively referred to as reactions leading to xylene loss. Also, in addition to the above described reactions, the xylene isomerization reactions occur simultaneously.

This new process comprises contacting an isomerization feed containing $C_8$ aromatics with an improved catalyst system, under conversion conditions including a temperature of from about 400° F. to about 1,000° F., a pressure of from about 0 to about 1,000 psig, a weight hourly space velocity (WHSV) of between about 0.1 and about 200 $hr^{-1}$, and a hydrogen, $H_2$, to hydrocarbon, HC, molar ratio of between 0.5 and about 10. Preferably, the conversion conditions include a temperature of from about 750° F. and about 900° F., a pressure of from about 50 and about 400 psig, a WHSV of between about 3 and about 50 $hr^{-1}$ and a $H_2$ to HC molar ratio of between about 1 and about 5.

The system of this invention comprises two catalysts. One of the catalysts, the first catalyst, is selective for ethylbenzene conversion while minimizing xylene loss. The other catalyst of the system, the second catalyst, isomerizes the xylenes to effect isomerization to the extent that the amount of para-xylene in the isomerization product is approximately equal to or greater than that at the thermal equilibrium of the xylene(s). In one embodiment of the process, the first catalyst will also show reduced activity for isomerization of the xylenes.

One embodiment of this invention is a process for isomerizing a feed which contains an aromatic $C_8$ mixture of ethylbenzene and xylene in which the para-xylene concentration is less than that at thermal equilibrium, which process comprises contacting the feed, under isomerization conditions, with a two catalyst system including a first catalyst and a second catalyst located in separate catalyst beds wherein the first catalyst comprises an intermediate pore size zeolite, e.g., ZSM-5, which has been modified by being exposed to at least one selectivation sequence, wherein the selectivation sequence includes the steps of contacting the zeolite with a selectivating agent and subsequently calcining the selectivated zeolite, said intermediate pore size zeolite further being combined with a silica binder; and the second catalyst comprises an intermediate pore size zeolite, e.g., ZSM-5, wherein the intermediate pore size zeolite is a small crystal size zeolite, and wherein said intermediate pore size zeolite is characterized by an alpha value of less than about 100;

whereby at least 30% of the ethylbenzene present in the aromatic $C_8$ mixture is converted to benzene, xylene, or to compounds readily removed by distillation from the aromatic $C_8$ mixture.

The modified zeolite mentioned above as being useful as the first catalyst typically comprises a silica bound intermediate pore size zeolite, e.g., ZSM-5, which has been coated with at least one coating, e.g., at least two coatings, e.g., at least 3 coatings, e.g., from 4 to 6 coatings, of a silicon selectivating agent, wherein each coating of selectivating agent is applied to the zeolite by a process comprising the steps of contacting the bound catalyst with a liquid organosilicon selectivating agent present in a liquid carrier and subsequently calcining the catalyst in an oxygen containing atmosphere. The carrier may be an organic liquid or it may be water or another aqueous solution. The zeolite may be combined with the silica binder before or after being coated with the selectivating agent. The zeolite may even be combined with the silica binder between subsequent coatings with the selectivating agent.

The intermediate pore size zeolite that is useful as the first catalyst typically comprises a medium or large crystal size zeolite.

Another embodiment of the invention includes a process of xylene isomerization by contacting a feed comprising an aromatic $C_8$ mixture of ethylbenzene and xylene in which the para-xylene concentration is less than that at thermal equilibrium, under isomerization conditions, with a two component catalyst system including the above mentioned modified intermediate pore size zeolite which has been further modified by steaming the modified intermediate pore size zeolite at moderate temperatures.

Yet another embodiment of the invention includes a process of xylene isomerization by contacting a feed comprising an aromatic $C_8$ mixture of ethylbenzene and xylene in which the para-xylene concentration is less than that at thermal equilibrium, under isomerization conditions, with a two component catalyst system including the above mentioned modified intermediate pore size zeolite which has been optionally further modified by steaming at moderate temperatures and that has been further modified by trim-selectivating the modified intermediate pore size zeolite. The trim-selectivation may be performed by coke trim-selectivating wherein an organic compound is decomposed in the presence of the modified intermediate pore size zeolite, at conditions suitable for decomposing the organic compound. Alternatively, the trim-selectivation may be performed by exposing the modified intermediate pore size zeolite to a reaction stream that includes a hydrocarbon to be converted and a trim-selectivating agent selected from a group of compounds including a large variety of silicon-containing compounds, under conditions suitable for trim-selectivating the zeolite.

Advantageously, the above described modified first catalysts have enhanced selectivity for ethylbenzene conversion while minimizing xylene loss. Accordingly, the isomerization process of the present invention exhibits increased selectivity for ethylbenzene conversion and may exhibit a capability for increased para-xylene production.

DETAILED DESCRIPTION OF THE INVENTION

Feedstock

In general, any aromatic $C_8$ mixture containing ethylbenzene and xylene may be used as feed to the process of this invention. Generally, such mixture will typically have an ethylbenzene content in the approximate range of 5 to 60 weight percent, an ortho-xylene content in the approximate range of 0 to 35 weight percent, a meta-xylene content in the approximate range of 20 to 95 weight percent and a paraxylene range of 0 to 15 weight percent. The feed in addition to the above aromatic $C_8$ mixture may contain non-aromatic hydrocarbons, i.e., naphthenes and paraffins in an amount up to 30 weight percent. In a preferred embodiment, the invention provides means to process a mixture of $C_8$ aromatics such as that derived from catalytic reforming of a petroleum naphtha to a mixture of reduced ethylbenzene content and increased content of para-xylene. The invention is particularly effective in treating a para-xylene lean mixture of $C_8$ aromatics to increase the para-xylene concentration up to approximately the thermal equilibrium level.

The catalyst of the present invention is especially suitable for the isomerization of $C_8$ aromatic streams that contain about 5 to 60 wt. % ethylbenzene, e.g., about 25 to 60 wt. % ethylbenzene. This range spans the range of ethylbenzene concentrations of streams that are derived from a reformer and a pyrolysis gasoline unit. The present catalyst may have high activity for cracking of normal and branched paraffins of the type present in unextracted $C_8$ aromatic streams.

Process Conditions

In accordance with the present invention, the above described feedstock is contacted with a catalyst system under conversion conditions of from about 400° F. to about 1,000° F., a pressure of from about 0 to about 1,000 psig, a weight hourly space velocity (WHSV) of between about 0.1 and about 200 $hr^{-1}$, and a hydrogen, $H_2$, to hydrocarbon, HC, molar ratio of between about 0.5 and about 10. Preferably, these conversion conditions include a temperature of from about 750° F. and about 900° F., a pressure of from about 50 and about 400 psig, a WHSV of between about 3 and about 50 $hr^{-1}$ and a $H_2$ to HC molar ratio of between about 1 and about 5. The WHSV is based on the weight of catalyst composition, i.e., the total weight of active catalyst and, if used, binder therefor.

The catalyst system used in accordance with the present invention is multifunctional. One function of the catalyst system is to effect isomerization of the xylene components to a concentration approximately equal to thermal equilibrium, while another function of the catalyst system is to convert ethylbenzene with minimal xylene loss. The ethylbenzene conversion products tend to be compounds that are more easily recovered or are more easily separated from the mixed xylenes. While the component effective for xylene isomerization is also somewhat effective for ethylbenzene conversion and the component effective for ethylbenzene conversion is also somewhat effective for xylene isomerization, a feature of this invention is that through the use of the two component catalyst system of this invention, the overall process of this invention produces para-xylene concentrations near thermal equilibrium while producing a more favorable ethylbenzene conversion to xylene loss ratio than processes using each component separately.

To effect high levels of conversion of ethylbenzene, while bringing the xylene components of the $C_8$ feed to thermal equilibrium in the isomerizer without excessive loss of xylenes to heavier aromatics and other components, the feed should be contacted with the two component catalyst system of this invention, under the conversion conditions described above. The conversion process described herein may be carried out as a batch type, semi-continuous or continuous operation. After use in a moving or fluidized bed reactor, the catalyst can be regenerated, in a regeneration zone in which the coke is burned from the catalyst in an oxygen containing atmosphere, e.g., air, at an elevated temperature after which the regenerated catalyst is recycled to the conversion zone for further contact with the charge stock. In a fixed bed reactor, regeneration can be carried out in a conventional manner by using initially an inert gas containing a small amount of oxygen (0.5 to 2 volume percent) to burn coke in a controlled manner so as to limit the temperature to a maximum of around about 450° C. to about 500° C.

In general, the xylene isomerization reaction is carried out in a fixed bed reactor containing the catalyst system described above. In a preferred embodiment, the two components of the catalyst system are in sequential beds. That is, the component of the catalyst system used in the process of the invention which is effective for ethylbenzene conversion forms a first bed, while the other component of the catalyst system, which is effective for xylene isomerization, forms a second bed. Thus, in theory, the conversion process of the invention could be carried out in two different reactors, possibly even at different process conditions. However, preferably, the feed is cascaded over the catalyst system disposed in sequential beds. In cascading, the feed is contacted with the two components of the catalyst system without intervening separation of light gases.

In embodiments below, the component of the catalyst system effective for ethylbenzene conversion is upstream with respect to the catalyst component which is effective to isomerize the xylene components of the $C_8$ aromatic feed. In this embodiment, the catalyst component which is effective for ethylbenzene conversion is employed in a volume sufficient to achieve the desired level of ethylbenzene conversion, generally a volume greater than about 10 percent, e.g., greater than about 25 percent, e.g., greater than about 50 percent, e.g., greater than about 55 percent, e.g., greater than about 60 percent, e.g., greater than about 75 percent, e.g., greater than about 80 percent of the volume of the total catalyst system.

After the conversion process, the isomerization product can be treated to isolate para-xylene and/or other desirable xylene(s). Thus, for example, the isomerizate product can be fed to a variety of para-xylene recovery units, such as a crystalizer, a membrane separation unit, or a selective adsorption unit, and thus the para-xylene may be isolated and recovered. The residual isomerizate can be stripped of products lighter than $C_8$. Products heavier than $C_8$ in the residual isomerizate can be further processed or may be fractionated out. $C_8$ fractions from which para-xylene has been removed can be recycled to the isomerizer.

One result of the process of this invention is to convert the mixed xylene components of the feed containing para-xylene in an amount less than that at thermal equilibrium to an extent such that product from the isomerizer contains para-xylene in an amount at least approaching that of para-xylene in the xylene mixture produced at thermal equilibrium.

Another result of the process of this invention is the conversion of a high proportion of the ethylbenzene contained in the mixed xylene feed. For example, ethylbenzene conversion levels of greater than about 30% are easily accomplished, e.g., greater than about 40%, e.g., greater than about 50%, e.g., greater than about 60%, e.g., greater than about 70%, e.g., greater than about 75%. Due to the unique properties of the catalyst system used as a part of this invention, this ethylbenzene conversion is accomplished with little xylene loss, for example xylene loss levels of about 2.5% are easily achieved, e.g., xylene loss levels of about 1.5%, e.g., xylene loss levels of about 1.0% may also be achieved.

Catalyst System

The foregoing results of the invention are typically realized by undertaking the isomerization using a system comprising two catalyst components. Each of these catalysts may be a multifunctional catalyst further comprising at least two components.

Each of these two catalyst components may be characterized by two common factors. Each may contain a strong hydrogenation/dehydrogenation component and each comprises a zeolite which is characterized by a Constraint Index within the approximate range of 1 to 12. Zeolites having a Constraint Index within the approximate range of 1 to 12 are often grouped as members of the class of zeolites referred to as shape selective.

Catalysts useful in this invention generally comprise an intermediate pore size zeolite (e.g., less than about 7 Angstroms pore size, such as from about 5 to less than about 7 Angstroms) having a silica to alumina molar ratio of at least about 5, specifically at least about 20. The silica to alumina ratio of at least one of the catalysts useful in the process in this invention, e.g., the first catalyst, may also optionally have an upper limit. If so limited, the silica to alumina molar ratio may be less than about 75, e.g., less than about 60, e.g., less than about 50, and e.g., less than about 40.

The silica to alumina ratio referred to may be determined by conventional analysis. This ratio is meant to represent, as closely as possible, the molar ratio in the rigid anionic framework of the zeolite crystal and to exclude silicon and aluminum in the binder or in cationic or other form within the channels.

Examples of intermediate pore size zeolites useful in this invention include ZSM-5 (U.S. Pat. No. 3,702,886 and Re. 29,948); ZSM-11 (U.S. Pat. No. 3,709,979); ZSM-12 (U.S. Pat. No. 3,832,449); ZSM-21 (U.S. Pat. No. 4,046,859); ZSM-22 (U.S. Pat. No. 4,556,477); ZSM-23 (U.S. Pat. No. 4,076,842); ZSM-35 (U.S. Pat. No. 4,016,245); ZSM-38 (U.S. Pat. No. 4,406,859); ZSM-48 (U.S. Pat. No. 4,397,827); ZSM-57 (U.S. Pat. No. 4,046,685); and ZSM-58 (U.S. Pat. No. 4,417,780). The entire contents of the above references are incorporated by reference herein.

An important characteristic of the crystal structure of the zeolites useful in this invention is that it provides constrained access to and egress from the intracrystalline free space by virtue of having an effective pore size intermediate between the small pore Linde A and the large pore Linde X, i.e. the pore windows of the structure typically have a size such as would be provided by 10-membered rings of oxygen atoms. It is to be understood, of course, that these rings are those formed by the regular disposition of the tetrahedra making up the anionic framework of the crystalline aluminosilicate, the oxygen atoms themselves being bonded to the silicon or aluminum atoms at the centers of the tetrahedra.

The intermediate pore size zeolites referred to herein have an effective pore size such as to freely sorb normal hexane. In addition, the structure must provide constrained access to larger molecules. It is sometimes possible to judge from a known crystal structure whether such constrained access exists. For example, if the only pore windows in a crystal are formed by 8-membered rings of oxygen atoms, then access to molecules of larger cross-section than normal hexane is excluded and the zeolite is not an intermediate pore size zeolite. Windows of 10-membered rings are preferred, although in some instances excessive puckering of the rings or pore blockage may render these zeolites ineffective.

The Constraint Index referred to above also qualifies the zeolite useful in this invention as having an intermediate pore size, as will be more fully described below.

Rather than attempt to judge from crystal structure whether or not a zeolite possesses the necessary constrained access to molecules larger than normal paraffins, a simple determination of the Constraint Index may be made. The method by which Constraint Index is determined is described fully in U.S. Pat. No. 4,016,218, incorporated herein by reference for details of the method. Constraint Index (CI) values for some typical zeolites including some which are suitable as catalysts in the process of this invention are as follows:

|  | CI (at test temperature) | |
|---|---|---|
| ZSM-4 | 0.5 | (316° C.) |
| ZSM-5 | 6–8.3 | (371° C.–316° C.) |
| ZSM-11 | 5–8.7 | (371° C.–316° C.) |
| ZSM-12 | 2.3 | (316° C.) |
| ZSM-20 | 0.5 | (371° C.) |
| ZSM-22 | 7.3 | (427° C.) |
| ZSM-23 | 9.1 | (427° C.) |
| ZSM-34 | 50 | (371° C.) |
| ZSM-35 | 4.5 | (454° C.) |
| ZSM-48 | 3.5 | (538° C.) |
| ZSM-50 | 2.1 | (427° C.) |
| MCM-22 | 0.6–1.5 | (399° C.–454° C.) |
| TMA Offretite | 3.7 | (316° C.) |
| TEA Mordenite | 0.4 | (316° C.) |
| Clinoptilolite | 3.4 | (510° C.) |
| Mordenite | 0.5 | (316° C.) |
| REY | 0.4 | (316° C.) |
| Amorphous Silica-alumina | 0.6 | (538° C.) |
| Dealuminized Y | 0.5 | (510° C.) |
| Erionite | 38 | (316° C.) |
| Zeolite Beta | 0.6–2.0 | (316° C.–399° C.) |

The above-described Constraint Index provides a definition of those zeolites which are useful in the process of the present invention. The very nature of this parameter and the above-referenced procedure by which it is determined, however, admits of the possibility that a given zeolite can be tested under somewhat different conditions and thereby exhibit different Constraint Indices. Constraint Index appears to vary somewhat with the severity of the conversion operation and the presence or absence of binder material. Similarly, other variables such as crystal size of the zeolite, the presence of occluded contaminants, etc., may affect the observed Constraint Index value. It will therefore be appreciated that it may be possible to select test conditions, e.g., temperature, as to establish more than one value for the Constraint Index of a particular zeolite. This explains the range of Constraint Indices for some zeolites, such as ZSM-5, ZSM-11, MCM-22, and Beta.

Generally, the zeolite, either directly or via initial ammonium exchange followed by calcination, is preferably hydrogen exchanged such that a predominant proportion of its exchangeable cations are hydrogen ions. In general, it is contemplated that more than 50 percent and preferably more than 75 percent of the cationic sites of the crystalline aluminosilicate zeolite will be occupied by hydrogen ions. ZSM-5 in the hydrogen exchanged form may be referred to herein as HZSM-5.

Original ions, e.g., alkali or alkaline earth metal, of the as-synthesized zeolite can be replaced in accordance with techniques well known in the art, at least in part, by ion exchange with other ions. Typical ion exchange techniques would be to contact the synthetic zeolite with a solution containing a salt of the desired replacing ion or ions. Examples of such salts include the halides, e.g., chlorides, nitrates and sulfates. Representative ion exchange techniques are disclosed in a wide variety of patents including U.S. Pat. Nos. 3,140,249; 3,140,251; and 3,140,253, each incorporated by reference herein.

As indicated above, each of the two catalyst components is a zeolite which may be associated with a hydrogenation-dehydrogenation component. Examples of such components include the oxide, hydroxide, sulfide, or free metal (i.e., zero valent) forms of Group VIII metals (i.e., Pt, Pd, Ir, Rh, Os, Ru, Ni, Co and Fe), Group IVB metals (i.e., Sn and Pb), Group VB metals (i.e., Sb and Bi), and Group VIIA metals (i.e., Mn, Tc and Re). Noble metals (i.e., Pt, Pd, Ir, Rh, Os and Ru) are preferred hydrogenation/dehydrogenation components. Combinations of catalytic forms of such noble or non-noble metal, such as combinations of Pt with Sn, may be used. The valence state of the metal is preferably in a reduced valence state, e.g., when this component is in the form of an oxide or hydroxide. The reduced valence state of this metal may be attained, in situ, during the course of a reaction, when a reducing agent, such as hydrogen, is included in the feed to the reaction.

The hydrogenation/dehydrogenation component may be incorporated into the catalyst by methods known in the art, such as ion exchange, impregnation or physical admixture. For example, solutions of appropriate metal salts may be contacted with the remaining catalyst components, either before or after selectivation of the catalyst, under conditions sufficient to combine the respective components. The metal containing salt is preferably water soluble. Examples of such salts include chloroplatinic acid, tetrammineplatinum complexes, platinum chloride, tin sulfate and tin chloride. The metal may be incorporated in the form of a cationic, anionic or neutral complex such as $Pt(NH_3)_4^{2+}$ and cationic complexes of this type will be found convenient for exchanging metals onto the zeolite. For example, a platinum modified catalyst can be prepared by first adding the catalyst to a solution of ammonium nitrate in order to convert the catalyst to the ammonium form. The catalyst is subsequently contacted with an aqueous solution of tetraamine platinum(II) nitrate or tetraamine platinum(II) chloride. Anionic complexes such as the vanadate or metatungstate ions are also useful for impregnating metals into the zeolites. Incorporation is preferably undertaken in accordance with the invention of U.S. Pat. No. 4,312,790, incorporated by reference herein. After incorporation of the metal, the catalyst can then be filtered, washed with water and calcined at temperatures of from about 250° C. to about 500° C.

The amount of hydrogenation/dehydrogenation component may be that amount which imparts or increases the catalytic ability of the overall catalyst to catalytically hydrogenate or dehydrogenate an organic compound under sufficient hydrogenation or dehydrogenation conditions. This amount is referred to herein as a catalytic amount. The amount of the hydrogenation-dehydrogenation component is suitably from about 0.001 to about 10 percent by weight, e.g., from about 0.1 to about 5 percent by weight, e.g., from about 0.1 to about 2 percent by weight, although this will, of course, vary with the nature of the component, less of the highly active noble metals, particularly platinum, being required than of the less active base metals.

In practicing the process of the invention, it may be desirable to formulate either or both of the catalysts of the invention with another material resistant to the temperature and other conditions of the process. Such matrix materials include synthetic or naturally occurring substances as well as inorganic materials such as clay, silica, and/or metal oxides. The preferred binder or support for the ethylbenzene conversion component is silica. Without intending to be bound thereby, it is believed that alumina binder catalyzed xylene isomerization reactions are further reduced through the use of inert silica binding for this catalyst. The metal oxides may be naturally occurring or in the form of gelatinous precipitates or gels including mixtures of silica and metal oxides. Naturally occurring clays which can be composited with the zeolite include those of the montmorillonite and kaolin families, which families include the subbentonites and the kaolins commonly known as Dixie, McNamee, Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the zeolites employed herein may be composited with a porous matrix material, such as alumina, silica-alumina, silica-magnesia, silica-zirconia, silica-thoria, silica-berylia, silica-titania, as well as ternary compounds such as silica-alumina-thoria, silica-alumina-zirconia, silica-alumina-magnesia, and silica-magnesia-zirconia. A mixture of these components could also be used. The matrix may be in the form of a cogel. The relative proportions of zeolite component and inorganic oxide gel matrix on an anhydrous basis may vary widely with the zeolite content ranging from between about 1 to about 99 percent by weight and more usually in the range of about 10 to about 80 percent by weight of the dry composite.

The form and the particle size of the catalyst are not critical to the present invention and may vary depending, for example, on the type of reaction system employed. Nonlimiting examples of the shapes of the catalyst which may be independently employed for either or both of the catalysts in the present invention include balls, pebbles, spheres, extrudates, channeled monoliths, honeycombed monoliths, microspheres, pellets or structural shapes, such as lobes, pills, cakes, honeycombs, powders, granules, and the like, formed using conventional methods, such as extrusion or spray drying. Where, for example, the final particles are designed for use as a fixed bed, the particles may preferably be formed into particles having a minimum dimension of at least about 0.01 inch and a maximum dimension of up to about one-half inch or one inch or more. Spherical particles having a diameter of about 0.03 inch to about 0.25 inch, preferably about 0.03 inch to about 0.15 inch, are often useful, especially in fixed bed or moving bed operations. With regard to fluidized bed systems, it is preferred that the major amount by weight of the particles have a diameter in the range of about 10 microns to about 250 microns, more preferably about 20 microns to about 150 microns.

The two components of the catalyst system of the invention differ from each other in two significant respects. Each will be characterized by different acidities and each will be characterized by different xylene diffusion properties.

Each of the components of the catalyst system will exhibit mutually exclusive xylene diffusional properties. These properties can be identified by noting the time (in minutes) required to sorb 30% of the equilibrium capacity of ortho-xylene at 120° C. and at an ortho-xylene partial pressure of 4.5±0.8 mm of mercury, a test described in U.S. Pat. Nos. 4,117,026; 4,159,282; and Re. 31,782; each of which is incorporated by reference herein. Herein, the equilibrium capacity of ortho-xylene is defined as greater than 1 gram of xylene(s) per 100 grams of zeolite. In accordance with the invention, the catalyst component effective for ethylbenzene conversion will have a value (in minutes) in excess of about 50 and preferably greater than about 100, but less than 10,000 minutes, while on the other hand, the isomerization component will require ortho-xylene sorption times of less than about 50 minutes and preferably less than about 10 minutes.

Ethylbenzene Conversion Component

The alpha value of the zeolite of the component of the catalyst system which is effective to convert ethylbenzene will typically be at least about 50. Generally, the alpha value of that component ranges from about 75 to about 500, and preferably, it ranges from about 100 to about 300. The xylene diffusion properties of this component are such that, under the process conditions described above, ethylbenzene conversion is favored over isomerization. As pointed out above, the zeolite of this component of the catalyst system is one characterized by a Constraint Index within the approximate range of 1 to 12. This parameter embraces a number of zeolites, some of which are described above. When, as in an embodiment described below, the zeolite of this component is ZSM-5, the requisite diffusional properties may be provided by providing ZSM-5 in medium and large size crystals as will be further described herein, which, optionally, have been further coated, as will be more fully described below, at least once, e.g., at least twice, e.g., at least three times, e.g., 4 to 6 times with a silicon selectivating agent described herein, wherein each coating of selectivating agent is applied to the zeolite by a process comprising the steps of contacting the zeolite with a liquid organosilicon selectivating agent present in a liquid carrier and subsequently calcining the catalyst in an oxygen containing atmosphere. As mentioned above, the zeolite may be bound with silica before being coated, after being coated or between successive coatings. Suitable selectivating agents are those which inhibit the diffusivity of the zeolite, particularly the diffusivity of the zeolite to ortho-xylene and meta-xylene.

For the purpose of this invention, ZSM-5 crystals may be divided by crystal size into at least 3 broad groups. These crystal sizes range from the small crystal size (e.g., about 0.03 to about 0.2µ, e.g., about 0.03 to about 0.05µ); medium crystal size (e.g., about 0.2 to about 1µ, e.g., about 0.2 to about 0.5µ); and large crystal size (e.g., greater than about 1µ, e.g., greater than about 2µ up to about 20µ). Recognizing that zeolite crystal size determination may be accomplished using a variety of methods, as will be further described below, a number of examples of methods to produce the various zeolite crystal sizes are listed. Crystals prepared by these methods may be used to define the different size groups. Examples of methods that may be used to prepare small crystal size ZSM-5 are given in U.S. Pat. Nos. 4,117,026 (Example 3); 4,526,879 (Examples 1, 2, 6, and 7); and 4,899,011 in Col. 9, lines 6–53. Examples of methods that may be used to prepare the medium crystal size ZSM-5 are given in U.S. Pat. Nos. 3,702,886 (Examples 2 and 26); 4,175,114; 4,199,556; 4,341,748; 4,375,458 (Examples 4 and 5); 5,243,117; and Great Britain Patent No. 1,581,513 (Examples 1 and 4). Examples of methods that may be used to prepare the large crystal size ZSM-5 include U.S. Pat. Nos. 3,702,886 (Example 27); 4,375,458 (all examples except 4, 5 and 16); 5,182,090 (Examples 1, 2, 14 through 24, and 26); and Great Britain Patent No. 1,581,513 (Examples 2 and 3). All of the above described patents are incorporated by reference herein.

The accurate direct measurement of the crystal size of zeolite materials is frequently very difficult. Microscopy methods, such as SEM and TEM, may be used, but these methods require measurements of a large number of crystals, and, for each crystal measured, values may be evaluated in up to three dimensions. Furthermore, in order to more completely characterize the crystal size of a batch of crystals, one should calculate the average crystal size as well as the degree of variance from this average in terms of a crystal size distribution.

If desired, rather than relying upon a complex evaluation of crystal size, crystal size may be expressed in terms of a calculated value of average crystal size obtained by measuring the rate of sorption of 2,2-dimethylbutane at 90° C. and 60 torr hydrocarbon pressure. The crystal size is computed by applying the diffusion equation given by J. Crank, *The Mathematics of Diffusion*, Clarendon Press, 52–56 (1957), for the rate of sorbate uptake by a solid whose diffusion properties can be approximated by a plane sheet model. In addition, the diffusion constant of 2,2-dimethylbutane, D, under these conditions, is taken to be $1.5 \times 10^{-14}$ cm$^2$/sec. The relation between crystal size measured in microns, d, and diffusion time measured in minutes, $t_{0.3}$, the time required for the uptake of 30% capacity of hydrocarbon, is:

$$d = 0.0704 \times t_{0.3}^{1/2}$$

One example of a large crystal material has a sorption time, $t_{0.3}$, of 497 minutes, which gives a calculated crystal size of 1.6 microns. One example of a small crystal material has a sorption time of 7.8 minutes, which gives a calculated size of 0.20 microns.

If ZSM-5 is the zeolite used as the ethylbenzene conversion component of this invention, it typically comprises a medium or large crystal size. If another intermediate pore size zeolite is used as the ethylbenzene conversion component, the crystal size may need to be adjusted from those given above for best performance.

Procedures for preparing silica bound ZSM-5 are described in U.S. Pat. Nos. 4,582,815; 5,053,374; and 5,182,242, incorporated by reference herein. A particular procedure for binding ZSM-5 with a silica binder involves an extrusion process.

A particular process for preparing silica bound ZSM-5 may comprise the steps of:

(a) mulling and then extruding a mixture comprising water, ZSM-5, colloidal silica and sodium ions under conditions sufficient to form an extrudate having an intermediate green strength sufficient to resist attrition during ion exchange step (b) set forth hereinafter;

(b) contacting the uncalcined extrudate of step (a) with an aqueous solution comprising ammonium cations under conditions sufficient to exchange cations in said ZSM-5 with ammonium cations; and (c) calcining the ammonium exchanged extrudate of step (b) under conditions sufficient to generate the hydrogen form of said ZSM-5 and increase the crush strength of said extrudate.

Another method of silica binding uses a suitable silicone resin, e.g., a high molecular weight, hydroxy functional silicone, such as Dow Corning Q6-2230 silicone resin in a method disclosed in U.S. Pat. No. 4,631,267, incorporated by reference herein. Other silicone resins that may be used in the method of this invention include those described in U.S. Pat. No. 3,090,691. When a silicone resin is used, a suitable polar, water soluble carrier, such as methanol, ethanol, isopropyl alcohol, N-methyl pyrrolidone or a dibasic ester may also be used along with water as needed. Dibasic esters that are useful in this invention include dimethyl glutarate, dimethyl succinate, dimethyl adipate, and mixtures thereof, one example of which is DuPont Chemical Co. DBE, which typically comprises about 50 to 75 percent dimethyl glutarate, 10 to 25 percent dimethyl adipate, 19 to 26 percent dimethyl succinate and less than about 0.2 wt. % methanol.

Extrusion aids may also be useful in the preparation of the catalysts of this invention. Methyl cellulose is a suitable extrusion aid, and one particular methyl cellulose that is effective as an extrusion aid in the method of this invention is a hydroxypropyl methyl cellulose, such as K75M Methocel™, available from Dow Chemical Co.

Various methods are known in the art for increasing the selectivity of zeolite catalysts. One such method is to modify the catalyst by treatment with a "selectivating agent." For example, U.S. Pat. Nos. 5,173,461; 4,950,835; 4,927,979; 4,465,886; 4,477,583; 4,379,761; 4,145,315; 4,127,616; 4,100,215; 4,090,981; 4,060,568; and 3,698,157 disclose specific methods for contacting a catalyst with a selectivating agent containing silicon ("silicon compound"). Also, U.S. application Ser. Nos. 08/069,251; 08/069,254; (now U.S. Pat. No. 5,367,099) 08/069,255 (now U.S. Pat. No. 5,403,800); 08/069,257; (now U.S. Pat. No. 5,382,737) 08/069,259; (now U.S. Pat. No. 5,365,004) and 08/069,260 (now U.S. Pat. No. 5,406,015); disclose methods for silicon selectivation of catalysts and use of those catalysts in toluene and ethylbenzene disproportionation. Each of the above patents and patent applications are incorporated by reference herein.

Traditionally, ex situ pre-selectivation of zeolites has involved single applications of the modifying compound. It may be noted, however, that the suggestion of multiple treatments was made in U.S. Pat. No. 4,283,306 to Herkes. The Herkes patent discloses the promotion of crystalline silica catalyst by application of an amorphous silica such as ethylorthosilicate (i.e., tetraethylorthosilicate). The Herkes patent contrasts the performance of catalyst treated once with an ethylorthosilicate solution followed by calcination against the performance of catalyst treated twice with ethylorthosilicate and calcined after each treatment. The Herkes disclosure shows that the twice-treated catalyst is less active and less selective than the once-treated catalyst as measured by methylation of toluene by methanol, indicating that the multiple ex situ selectivation confers no benefit and in fact reduces a catalyst's efficacy in shape-selective reactions.

The present catalyst may be selectivated by more than one selectivation method. In accordance with one selectivation method, the catalyst is selectivated by one or more treatments with a liquid organosilicon compound in a liquid carrier, each treatment being followed by calcination of the treated material in an oxygen containing atmosphere, e.g., air. More particularly, for example, with reference to the above-mentioned steps (a)–(c), this first selectivation method may involve the additional steps of:

(d) contacting the calcined extrudate of step (c) with a liquid comprising a liquid carrier and at least one organosilicon selectivating agent having at least two silicon atoms per molecule under conditions sufficient to incorporate said organosilicon selectivating agent in the extrudate, (e) calcining the extrudate of step (d) under conditions sufficient to decompose said organosilicon selectivating agent and to remove any residue of said liquid carrier from said extrudate; and, optionally, (f) repeating selectivation steps (d) and (e) at least once.

Another method for selectivating the silica bound ZSM-5 involves passing a feed stream comprising toluene, hydrogen and an organosilicon compound over said silica bound ZSM-5 under conditions sufficient to deposit a residue of organosilicon compound on said silica bound ZSM-5.

The above-mentioned first method for selectivating the zeolite, wherein the zeolite, e.g., ZSM-5, is treated by multiple impregnation treatments, is referred to herein as the multiple impregnation method. The above-mentioned second method for selectivating the zeolite, wherein the zeolite, e.g., ZSM-5, is treated under trim-selectivation conditions, is referred to herein as the trim-selectivation method.

In accordance with the multiple impregnation method, the zeolite, e.g., ZSM-5, is treated at least once, e.g., at least twice, e.g., at least 3 times, e.g., from 4 to 6 times, with a liquid medium comprising a liquid carrier and at least one liquid organosilicon compound. The organosilicon compound may be present in the form of a solute dissolved in the liquid carrier or in the form of emulsified droplets in the liquid carrier. The liquid carrier may be water, an organic liquid or a combination of water and an organic liquid. Particularly when the liquid medium comprises an emulsion of the organosilicon compound in water, the liquid medium may also comprise an emulsifying agent, such as a surfactant. As mentioned above, the zeolite may be silica bound before selectivation, after selectivation, or between successive selectivation coatings.

Various organic compounds have been employed as carriers for silicon compounds in the silicon impregnation methods applied to zeolite catalysts. For example, U.S. Pat. Nos. 4,145,315; 4,127,616; 4,090,981; and 4,060,568 describe the use of inter alia $C_{5-7}$ alkanes as solvents for silicon impregnation. When the catalyst is impregnated with an organosilicon compound included in an organic carrier, the organic carrier may be any organic compound or mixture of organic compounds which are capable of dissolving or otherwise suitably suspending the organosilicon compound. Such organic carriers may be hydrocarbons, such as linear, branched, and cyclic hydrocarbons having five or more, especially 7 or more, carbon atoms per molecule, e.g., alkanes, such as heptane, octane, nonane, and undecane. The boiling point of the organic compound, e.g., alkane, may be greater than about 70° C.. Mixtures of low volatility organic compounds, such as hydrocracker recycle oil, may be employed as carriers. Particularly preferred organic carriers are decane and dodecane.

The organosilicon compound which is used to selectivate the zeolite may be a silicone or a silane. Silicones are defined herein as those compounds wherein silicon atoms are bonded to one another via oxygen atoms. Silanes are defined herein as those compounds wherein silicon atoms are bonded directly to one another.

The silicone compound which may be used to selectivate the present zeolite may be considered to be constructed of a siloxy backbone structure capped with terminal groups. This siloxy backbone structure may be a chain structure represented by the formula

where p is from 1 to 9. This siloxy backbone structure may also be a cyclic structure represented by the formula

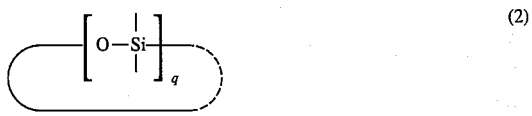

where q is from 2 to 10. Branched chain structures and composite chain/cyclic structures are also possible for the siloxy backbone of the silicone selectivating agent.

The hydrocarbyl groups which cap the available bonds of the siloxy backbone may have from 1 to 10 carbon atoms. Examples of such hydrocarbyl groups are methyl and phenyl.

Examples of silicone compounds having a chain siloxy backbone structure include those of the formula

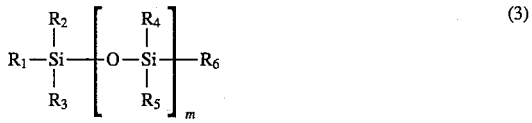

where $R_1$ and $R_6$ are independently hydrogen, methyl, or phenyl; $R_2$, $R_3$, $R_4$, and $R_5$ are independently methyl or phenyl; and m is from 1 to 10, e.g., from 1 to 4. Preferably, no more than one phenyl group is bonded to each silicon atom. Particular examples of such silicone compounds having a chain siloxy backbone structure include hexamethyldisiloxane, decamethyltetrasiloxane and diphenyltetramethyldisiloxane. Particular examples of silicone compounds having a cyclic siloxy backbone structure include octamethylcyclotetrasiloxane and decamethylcyclopentasiloxane. Particular examples of silicone compounds having a branched siloxy backbone structure are tris-(trimethylsiloxy)-phenylsilane and tris-(trimethylsiloxy)-silane.

The silane compounds, useful as selectivating agents according to the present method, may have structures corresponding to the above-mentioned silicone compounds, wherein the silicon atoms are bonded directly to one another instead of via oxygen atoms. Examples of silanes having a chain backbone structure include those of the formula

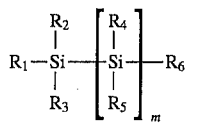    (4)

where $R_1$ and $R_6$ are independently hydrogen, methyl, or phenyl; $R_2$, $R_3$, $R_4$, and $R_5$ are independently methyl or phenyl; and m is from 1 to 10, e.g., from 1 to 4. An example of such a silane compound is hexamethyldisilane.

The present zeolite may be selectivated by more than one selectivation method. In particular, prior to use in the present process, the zeolite may be contacted with an organosilicon compound, followed by calcination in an oxygen containing atmosphere. Such a pretreatment of the zeolite is referred to herein as a preselectivation treatment.

In accordance with an example of a preselectivation method, the catalyst is preselectivated by single or multiple treatments with a liquid organosilicon compound in a liquid carrier, each treatment being followed by calcination of the treated material in an oxygen containing atmosphere, e.g., air.

In accordance with the multiple impregnation preselectivation method, the zeolite is treated at least twice, e.g., at least 3 times, e.g., from 4 to 6 times, with a liquid medium comprising a liquid carrier and at least one liquid organosilicon compound. The organosilicon compound may be present in the form of a solute dissolved in the liquid carrier or in the form of emulsified droplets in the liquid carrier. For the purposes of the present disclosure, it will be understood that a normally solid organosilicon compound will be considered to be a liquid (i.e., in the liquid state) when it is dissolved or emulsified in a liquid medium. The liquid carrier may be water, an organic liquid or a combination of water and an organic liquid. Particularly when the liquid medium comprises an emulsion of the organosilicon compound in water, the liquid medium may also comprise an emulsifying agent, such as a surfactant.

The organosilicon compound preselectivating agent may be, for example, a silicone, a siloxane, a silane or mixtures thereof. These organosilicon compounds may have at least 2 silicon atoms per molecule. These organosilicon compounds may be solids in pure form, provided that they are soluble or otherwise convertible to the liquid form upon combination with the liquid carrier medium. The molecular weight of the silicone, siloxane or silane compound employed as a preselectivating agent may be between about 80 and about 20,000, and preferably within the approximate range of 150 to 10,000. Representative preselectivation silicone compounds include dimethyl silicone, diethyl silicone, phenylmethyl silicone, methylhydrogen silicone, ethylhydrogen silicone, phenylhydrogen silicone, methylethyl silicone, phenylethyl silicone, diphenyl silicone, methyltrifluoropropyl silicone, ethyltrifluoropropyl silicone, polydimethyl silicone, tetrachlorophenylmethyl silicone, tetrachlorophenylethyl silicone, tetrachlorophenylhydrogen silicone, tetrachlorophenylphenyl silicone, methylvinyl silicone, and ethylvinyl silicone. The preselectivating silicone, siloxane or silane compound need not be linear, but may be cyclic, for example, hexamethyl cyclotrisiloxane, octamethyl cyclotetrasiloxane, hexaphenyl cyclotrisiloxane and octaphenyl cyclotetrasiloxane. Mixtures of these compounds may also be used as preselectivating agents, as may silicones with other functional groups.

Preferred organosilicon preselectivating agents, particularly when the preselectivating agent is dissolved in an organic carrier or emulsified in an aqueous carrier, include dimethylphenyl methyl polysiloxane (e.g., Dow-550) and phenylmethyl polysiloxane (e.g., Dow-710). Dow-550 and Dow-710 are available from Dow Chemical Co., Midland, Mich.

When the organosilicon preselectivating agent is present in the form of a water soluble compound in an aqueous solution, the organosilicon may be substituted with one or more hydrophilic functional groups or moieties, which serve to promote the overall water solubility of the organosilicon compound. These hydrophilic functional groups may include one or more organoamine groups, such as —$N(CH_3)_3$, —$N(C_2H_5)_3$ and —$N(C_3H_7)_3$. A preferred water soluble organosilicon preselectivating agent is an n-propylamine silane, available as Hydrosil 2627 from Huls America.

When the zeolite is preselectivated by a single or multiple impregnation technique, the zeolite is calcined after each impregnation to remove the carrier and to convert the liquid organosilicon compound to a solid residue material thereof. This solid residue material is referred to herein as a siliceous solid material, insofar as this material is believed to be a polymeric species having a high content of silicon atoms in the various structures thereof. However, this siliceous solid residue material may also comprise carbon atoms in the structure thereof, resulting from the residue of the organo portion of the organosilicon compound used to impregnate the catalyst.

Following each impregnation, the zeolite may be calcined at a rate of from about 0.2° C./minute to about 5° C./minute to a temperature greater than 200° C., but below the temperature at which the crystallinity of the zeolite is adversely affected. This calcination temperature may be below 600° C., e.g., within the approximate range of 350° C. to 550° C. The duration of calcination at the calcination temperature may be from 1 to 24 hours, e.g., from 2 to 6 hours.

The impregnated zeolite may be calcined in an inert or oxidizing atmosphere. An example of such an inert atmosphere is a nitrogen, i.e., $N_2$, atmosphere. An example of an oxidizing atmosphere is an oxygen containing atmosphere, such as air. Calcination may take place initially in an inert, e.g., $N_2$, atmosphere, followed by calcination in an oxygen containing atmosphere, such as air or a mixture of air and $N_2$. Calcination should be performed in an atmosphere substantially free of water vapor to avoid undesirable uncontrolled steaming of the zeolite. The zeolite may be calcined once or more than once following each impregnation. The various calcinations following each impregnation need not be identical, but may vary with respect to the temperature, the rate of temperature rise, the atmosphere and the duration of calcination.

The amount of siliceous residue material which is deposited on the zeolite or bound zeolite is dependent upon a number of factors including the temperatures of the impregnation and calcination steps, the concentration of the organosilicon compound in the carrying medium, the degree to which the catalyst has been dried prior to contact with the organosilicon compound, the atmosphere used in the calcination and duration of the calcination.

Preferably, the kinetic diameter of both the organosilicon compound, which is used to preselectivate the zeolite, and the organosilicon compound (e.g., silicone compound), which is used to functionalize the zeolite, is larger than the zeolite pore diameter, in order to avoid entry of the organosilicon compound into the zeolite pores and any concomitant reduction in the internal activity of the zeolite.

Particular water soluble organosilicon compounds, which may be used for multiple impregnations of the present catalyst, are referred to as amino silane polymers in U.S. application Ser. No. 08/042,430, filed Apr. 5, 1993, (now U.S. Pat. No. 5,371,312) incorporated by reference herein.

As mentioned previously herein, aqueous emulsions of organosilicon compounds comprising surfactants may be used for the impregnation of the present catalyst. Stable aqueous emulsions of organosilicon compounds (e.g., silicone oil) are described in U.S. application Ser. No. 08/141, 758, filed Oct. 27, 1993, now abandoned, incorporated by reference herein.

After the impregnation/calcination sequence, the catalyst may be subjected to steaming conditions sufficient to increase the activity and/or selectivity of the catalyst. Such conditions are disclosed in U.S. application Ser. No. 08/042, 431, filed Apr. 5, 1993, (now U.S. Pat. No. 5,349,114) incorporated by reference herein. The steaming conditions may include a temperature of from about 100° C. to about 600° C., e.g., from about 175° C. to about 325° C., with from about 1% to about 100% steam, e.g., from about 50% to about 100% steam, at a pressure of from about 0.01 psia to about 50 psia, and for a duration of about 0.1 to about twenty-four hours, e.g., from about three to about six hours. Excessive steaming or steaming under too severe conditions may be detrimental to the activity and selectivity of the catalyst.

In accordance with the trim-selectivation method described herein, the catalyst is contacted with a feed stream typically comprising toluene, hydrogen and organosilicon compound under suitable trim selectivation conditions. These conditions may include a temperature ranging from about 100° C. to about 600° C., e.g., from about 300° C. to about 500° C., a pressure ranging from about 0 to about 2000 psig, e.g., from about 15 to about 800 psig, a mole ratio of hydrogen to hydrocarbons (e.g., toluene) from about 0.1 to 20, e.g., from about 0.1 to 10, e.g., from about 1 to about 4, and a weight hourly space velocity (WHSV) from about 0.1 to about 100 $hr^{-1}$, e.g., from about 0.1 to about 10 $hr^{-1}$. Toluene may comprise about 50 wt. % to 100 wt. at least 80 wt. %, of the hydrocarbons in the feedstock Other hydrocarbons, such as benzene, xylenes and trimethylbenzenes, may also be present in the trim-selectivation feedstock.

The presence of a sufficient amount of hydrogen in the trim-selectivation feedstock is necessary to prevent rapid aging of the catalyst during the selectivation process resulting in an excessive reduction in the catalyst activity, possibly accompanied by a reduction in selectivity for ethylbenzene conversion. This rapid aging is believed to result from a rapid build-up of excessive amounts of carbonaceous deposits (i.e., coke), which may even extend into the pore system of the zeolite in the catalyst. However, even when hydrogen is used in optimal fashion to prevent aging during the selectivation process, a small amount of carbonaceous deposit forms on the catalyst. As a result of this carbonaceous deposit, the elemental analysis of the trim-selectivated catalyst reveals a carbon content significantly greater than the carbon content of the fresh catalyst prepared by the multiple impregnation method described herein. More particularly, the trim-selectivated catalyst may contain at least 2 wt. %, e.g., at least 4 wt. %, of carbon by elemental analysis, whereas the catalyst prepared by the multiple impregnation method may contain less than 0.5 wt. % of carbon as measured by elemental analysis. These weight percentages are expressed in terms of the weight of the entire catalyst including the zeolite, binder and optional components, such as hydrogenation/dehydrogenation components.

The present catalyst, prepared by whatever method, e.g., the multiple impregnation technique or the trim-selectivation technique, may also be subjected to controlled coking. This controlled coking procedure is also referred to herein as coke selectivation. This optional coke selectivation may involve contacting the catalyst with a thermally decomposable organic compound at an elevated temperature in excess of the decomposition temperature of said compound but below the temperature at which the crystallinity of the zeolite is adversely affected. This contact temperature may be, for example, less than about 650° C.

Organic materials, which may be used for this coke selectivation process, encompass a wide variety of compounds including by way of example, hydrocarbons, such as paraffins, cycloparaffins, olefins, cycloolefins and aromatics; oxygen-containing organic compounds, such as alcohols, aldehydes, ethers, ketones and phenols; and heterocyclics, such as furans, thiophenes, pyrroles and pyridines. A hydrogen cofeed may be used to deter the excessive build-up of coke. Further details regarding coke selectivation techniques are provided in the U.S. Pat. No. 4,117,026, as well as in U.S. application Ser. No. 08/069,251, filed May 28, 1993, incorporated by reference herein. An organosilicon cofeed may be, optionally, included along with the organic material feed used for coke selectivation. This organosilicon material may be selected from the organosilicon compounds mentioned hereinabove for use in the trim-selectivation of the catalyst.

While not wishing to be bound by any theory, it is theorized that the extreme selectivity of the present catalyst is obtained by rendering acid sites on the external surfaces of the zeolite substantially inaccessible to reactants, while possibly increasing the tortuosity of the zeolite pore system.

Isomerization Component

The other component of the catalyst system is effective to isomerize the xylenes of the feed containing $C_8$ aromatics. This component of the catalyst system will typically comprise an intermediate pore size zeolite, e.g., one having a Constraint Index between 1 and 12, specifically ZSM-5. The acidity of the ZSM-5 of this component, expressed as the alpha value, may be less than about 150, e.g., less than about 100, e.g., at most 50, e.g., the alpha value will range from about 5 to about 25. Small crystal size zeolites, as defined herein, will typically be used in this component.

When alpha value is examined, it is noted that the alpha value is an approximate indication of the catalytic cracking activity of the catalyst compared to a standard catalyst and it gives the relative rate constant (rate of normal hexane conversion per volume of catalyst per unit time). It is based on the activity of silica-alumina cracking catalyst taken as an alpha of 1 (rate constant is 0.016 $sec^{-1}$). The alpha test is described in U.S. Pat. No. 3,354,078; in the *Journal of Catalysis*, Vol. 4, p. 527 (1965); Vol. 6, p. 278 (1966); and Vol. 61, p. 395 (1980), each incorporated herein by reference as to that description. The experimental conditions of the test used herein include a constant temperature of 538° C. and a variable flow rate as described in detail in the *Journal of Catalysis*, Vol. 61, p. 395. The higher alpha values correspond with a more active cracking catalyst.

EXAMPLE 1

Preparation of a ZM-5 Isomerization Catalyst

An alumina bound, platinum impregnated catalyst was prepared based upon small crystal size ZSM-5. This catalyst, which was not silicon selectivated, will be referred to as Catalyst A.

EXAMPLE 2

Preparation of a Silica Bound ZSM-5 Catalyst

A silica bound ZSM-5 catalyst was prepared by combining a medium crystal size ZSM-5, precipitated and colloidal silica according to the method disclosed in U.S. Pat. No. 5,053,374. This catalyst will be referred to as Catalyst B.

EXAMPLE 3

Preparation of a Silica Bound ZSM-5 Catalyst

A silica bound medium crystal size ZSM-5 catalyst prepared by the same method as Example 2 was contacted with a solution containing dimethylphenylmethyl polysiloxane (Dow-550) dissolved in decane. The catalyst was calcined at 538° C. in nitrogen followed by air, then was treated with the silane dimethylphenylmethyl polysiloxane/decane solution again, and was calcined a second time. This catalyst will be referred to as Catalyst C.

EXAMPLE 4

Comparison of Catalyst Conversion Activity

Catalysts A, B, and C, as prepared above, were tested for 15 days using a paraxylene depleted, mixed xylene feed at 30 psig and at a weight hourly space velocity of 6 hr$^{-1}$. The data have been normalized to reflect a 30% ethylbenzene conversion level. Results of this comparison test are shown in Table 1 below.

TABLE 1

|  | Catalyst A | Catalyst B | Catalyst C |
| --- | --- | --- | --- |
| Normalized Avg. Temperature, °F. | 650 | 680 | 725 |
| Xylene Loss, wt. % | 2.4 | 1.4 | 1.1 |
| Para-xylene Approach to Equilibrium, wt. % | 100.8 | 99.8 | 91.6 |
| (MEB + TMB + DMEB)/ DEB, wt. % | 1.9 | 0.9 | 0.9 |

What is claimed is:

1. A process for isomerizing xylenes in a feed containing ethylbenzene and xylenes, wherein the para-xylene concentration is less than that at thermal equilibrium, said process comprising the steps of:
   (a) contacting said feed under ethylbenzene conversion conditions with a first bed of a first catalyst comprising a silica binder and an intermediate pore size zeolite, wherein said first catalyst requires at least 50 minutes to sorb 30% of the equilibrium capacity of ortho-xylene at 120° C. and at an ortho-xylene partial pressure of 4.5±0.8 mm of mercury, wherein the intermediate pore size zeolite of the first catalyst has been modified by being exposed to at least one selectivation sequence, said selectivation sequence comprising the steps of contacting the zeolite with a selectivating agent and subsequently calcining the selectivated zeolite; and
   (b) contacting the effluent from step (a) under xylene isomerization conditions with a second bed of a second catalyst comprising an intermediate pore size zeolite, wherein said second catalyst requires less than 50 minutes to sorb 30% of the equilibrium capacity of ortho-xylene at 120° C. and at an ortho-xylene partial pressure of 4.5±0.8 mm of mercury.

2. The process according to claim 1, wherein the first catalyst requires at least 100 minutes to sorb 30% of the equilibrium capacity of ortho-xylene at 120° C. and at an ortho-xylene partial pressure of 4.5±0.8 mm of mercury.

3. The process according to claim 2, wherein the second catalyst requires less than 10 minutes to sorb 30% of the equilibrium capacity of ortho-xylene at 120° C. and at an ortho-xylene partial pressure of 4.5±0.8 mm of mercury.

4. The process according to claim 3, wherein the second catalyst comprises an alumina binder.

5. The process according to claim 1, wherein ethylbenzene conversion and xylene isomerization conditions independently comprise a temperature of from about 400° F. to about 1,000° F., a pressure of from about 0 to 1,000 psig, a weight hourly space velocity (WHSV) of between 0.5 and 100 hr$^{-1}$, and a H$_2$/HC mole ratio of between about 0.5 and about 10.

6. The process according to claim 1 wherein the intermediate pore size zeolite of the first catalyst has been modified by being exposed to at least two selectivation sequences.

7. The process according to claim 1 wherein the selectivating agent used to modify the first catalyst is present in an organic carrier.

8. The process according to claim 7 wherein the organic carrier is selected from the group consisting of linear hydrocarbon, branched hydrocarbon, cyclic hydrocarbon and mixtures thereof.

9. The process according to claim 1 wherein the selectivating agent used to modify the first catalyst is present in an aqueous carrier.

10. The process of claim 1, wherein the selectivating agent is selected from the group consisting of silicones, silanes, siloxanes, organoamine silane polymers and mixtures thereof.

11. The method of claim 1, wherein the selectivating agent is selected from the group consisting of (a)

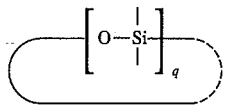

where q is from 2 to 10; (b)

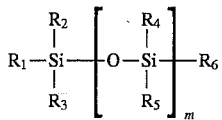

where R$_1$ and R$_6$ are independently hydrogen, methyl, or phenyl; R$_2$, R$_3$, R$_4$, and R$_5$ are independently methyl or phenyl; and m is from 1 to 10; and (c)

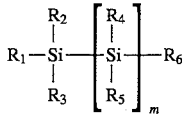

where R$_1$ and R$_6$ are independently hydrogen, methyl, or phenyl; R$_2$, R$_3$, R$_4$, and R$_5$ are independently methyl or phenyl; and m is from 1 to 10.

12. The process of claim 1, wherein the selectivating agent comprises dimethylphenyl polysiloxane.

13. The process of claim 1, wherein the selectivating agent comprises n-propylamine silane.

14. The process of claim 1, wherein the intermediate pore size zeolite of the first catalyst is combined with the silica binder before being modified.

15. The process of claim 1, wherein the intermediate pore size zeolite of the first catalyst is combined with the silica binder after being modified.

16. The process of claim 1, wherein the intermediate pore size zeolite of the first catalyst is modified in an as-synthesized condition.

17. The process of claim 1, wherein the modified intermediate pore size zeolite of the first catalyst is steamed under conditions comprising from about 1% to about 100% water vapor, a temperature of from about 100° C. to about 600° C., a pressure of from about 0.01 to about 50 psia, for a time of from about 0.1 to about 24 hours.

18. The process according to claim 1 wherein the intermediate pore size zeolite of the first catalyst is silica bound by a sequence of steps comprising
   (a) mulling and then extruding a mixture comprising water, the intermediate pore size zeolite, colloidal silica and sodium ions under conditions sufficient to form an extrudate having an intermediate green strength sufficient to resist attrition during ion exchange step (b) set forth hereinafter;
   (b) contacting the extrudate of step (a) with an aqueous solution comprising ammonium cations under conditions sufficient to exchange cations in said intermediate pore size zeolite with ammonium cations;
   (c) calcining the ammonium exchanged extrudate of step (b) under conditions sufficient to generate a hydrogen form of said intermediate pore size zeolite and increase the crush strength of said extrudate.

19. The process according to claim 18 wherein the silica bound intermediate pore size zeolite is modified by a selectivation sequence comprising the additional steps of
   (d) contacting the calcined extrudate of step (c) of claim 19 with a liquid comprising a liquid carrier and at least one organosilicon selectivating agent having at least two silicon atoms per molecule under conditions sufficient to incorporate said organosilicon selectivating agent in the extrudate,
   (e) calcining the extrudate of step (d) under conditions sufficient to decompose said organosilicon selectivating agent and to remove any residue of said liquid carrier from said extrudate; and, optionally,
   (f) repeating selectivation steps (d) and (e) at least once.

20. The process according to claim 1 wherein the intermediate pore size zeolite of the first catalyst further comprises a silica to alumina molar ratio of less than about 75 to 1.

21. The process of claim 1, wherein the intermediate pore size zeolite of the first catalyst comprises a zeolite having a constraint index of 1 to 12.

22. The process of claim 1, wherein the intermediate pore size zeolite of the first catalyst is selected from the group consisting of ZSM-5, ZSM-11, ZSM-12, ZSM-21, ZSM22, ZSM-23, ZSM-35, ZSM-38, ZSM-48, ZSM-57, and ZSM-58.

23. The process of claim 1, wherein the intermediate pore size zeolite of the first catalyst is ZSM-5.

24. The process of claim 23, wherein the intermediate pore size zeolite of the first catalyst comprises a medium or large crystal size.

25. The process of claim 23, wherein the intermediate pore size zeolite of the first catalyst comprises a medium crystal size.

26. The process of claim 1, wherein the intermediate pore size zeolite of the second catalyst comprises a zeolite having a constraint index of 1 to 12.

27. The process of claim 1, wherein the intermediate pore size zeolite of the second catalyst is selected from the group consisting of ZSM-5, ZSM-11, ZSM-12, ZSM-21, ZSM22, ZSM-23, ZSM-35, ZSM-38, ZSM-48, ZSM-57, and ZSM-58.

28. The process of claim 1, wherein the intermediate pore size zeolite of the second catalyst is ZSM-5.

29. The process of claim 1, wherein the second catalyst contains an ion selected from the group consisting of hydrogen, hydrogen precursor, metals of Periodic Table Group VIII, and combinations thereof.

30. The process of claim 24, wherein the ion contained on the second catalyst comprises platinum.

31. The process of claim 1, wherein the intermediate pore size zeolite of the second catalyst has an alpha value of less than about 100.

32. The process of claim 1, wherein the first catalyst contains an ion selected from the group consisting of hydrogen, hydrogen precursor, metals of Periodic Table Group VIII, and combinations thereof.

33. The process of claim 32, wherein the ion contained on the first catalyst comprises platinum.

34. The process of claim 1, wherein the first catalyst and the second catalyst are located in the same reactor, and wherein the feed contacts the first catalyst before contacting the second catalyst.

35. The process of claim 1, wherein the first catalyst and the second catalyst are located in separate reactors, and wherein the feed contacts the first catalyst before contacting the second catalyst.

36. The process of claim 1, wherein the volume of the first catalyst comprises at least 50 percent of the sum of the volumes of the first catalyst and the second catalyst.

37. The process of claim 1, wherein the volume of the first catalyst comprises at least 75 percent of the sum of the volumes of the first catalyst and the second catalyst.

38. A process for isomerizing a feed which contains an aromatic $C_8$ mixture of ethylbenzene and xylene in which the para-xylene concentration is less than that at thermal equilibrium, which process comprises contacting the feed, under isomerization conditions, with a two component catalyst system including a first catalyst and a second catalyst located in separate catalyst beds
wherein
   the first catalyst comprises ZSM-5 which has been modified by being exposed to at least one selectivation sequence, wherein the selectivation sequence includes the steps of contacting the ZSM-5 with a selectivating agent in a carrier and subsequently calcining the selectivated ZSM-5, said ZSM-5 comprising a medium or large crystal size zeolite, said ZSM-5 being silica bound, said first catalyst comprising a hydrogenation component; and
   the second catalyst comprises a small crystal size ZSM-5, and wherein the ZSM-5 has an alpha value of less than about 150, said second catalyst comprising a hydrogenation component;
   whereby at least 30% of the ethylbenzene present in the aromatic $C_8$ mixture is converted to benzene, xylene, or to compounds readily removed by distillation from the aromatic $C_8$ mixture.

39. The process of claim 38, wherein the ZSM-5 of the first catalyst has been modified by being exposed to at least two selectivation sequences.

40. The process of claim 38, wherein at least 50% of the ethylbenzene present in the aromatic $C_8$ mixture is converted to benzene, xylene, or to compounds readily removed by distillation from the aromatic $C_8$ mixture.

* * * * *